United States Patent [19]

Tanaka et al.

[11] Patent Number: 4,990,457
[45] Date of Patent: Feb. 5, 1991

[54] WHOLE BLOOD DRY ANALYSIS ELEMENT
[75] Inventors: Mitsutoshi Tanaka; Takaki Arai, both of Saitama, Japan
[73] Assignee: Fuji Photo Film Co., Ltd., Kanagawa, Japan
[21] Appl. No.: 333,430
[22] Filed: Apr. 4, 1989
[30] Foreign Application Priority Data
  Apr. 5, 1988 [JP] Japan .................................. 63-83679
[51] Int. Cl.$^5$ ............................................ G01N 31/22
[52] U.S. Cl. .................................... 436/170; 422/56; 422/57; 422/58; 435/805; 436/63; 436/70; 436/169
[58] Field of Search .................................... 422/56–58; 436/63, 70, 169, 170; 435/805

[56] References Cited
U.S. PATENT DOCUMENTS
4,777,139 10/1988 Wong et al. ...................... 436/10 X Primary Examiner—Robert J. Warden
Assistant Examiner—Jill Johnston
Attorney, Agent, or Firm—McAulay Fisher Nissen & Goldberg

[57] ABSTRACT

A dry analysis element for determination of a particular constituent in erythrocyte-containing blood, which comprises at least a water permeable porous spreading layer and a water permeable reagent layer arranged on the side opposite to the liquid accepting face of the porous spreading layer, and which contains a reagent composition capable of producing an optically detectable substance in the presence of an analyte in at least either of the water permeable layers. The porous spreading layer contains cholic acid, deoxycholic acid or salts thereof to enable accurate determination of the constituents in whole blood, irrespective of the hematocrit value.

18 Claims, No Drawings

WHOLE BLOOD DRY ANALYSIS ELEMENT

FIELD OF THE INVENTION

This invention relates to a dry chemical analysis element to be used for quantitative analysis of a particular substance in blood.

FIELD OF THE INVENTION

Quantitative analyses of various metabolic components present in body fluid, e.g., glucose, bilirubin, uric acid, cholesterol, lactate dehydrogenase, creatine kinase, GOT, GPT, and the like, are of importance in clinics, and indispensable to the diagnoses of diseases, following the progress of recovery, judging the prognosis, and so on. In the clinical chemical inspection using blood and the like as a sample, it is desirable that the inspection should be performed with high accuracy using a small amount of liquid sample. Hitherto, wet analyses using solution samples have been widely employed. However, they do not allow for rapidity of the analyses.

Also, methods for clinical analysis which utilize a substantially dry analytical element are known, e.g., a sample piece or a multilayer analytical element having an analytical reagent system. The dry chemical analyses are superior to chemical analyses utilizing wet processes, i.e., methods in which a reagent is used in a solution state with respect to simplicity in practical use, cost economy and rapidity of analysis. Dry multilayer analytical elements have been developed as a means of effecting rapid, accurate analyses using a small amounts of liquid sample. They are reported, e.g., in JP-B-No. 53-21677 (The term "JP-B" as used herein means an "examined Japanese patent publication"), JP-A-No. 55-164356 and JP-A-No. 60-222769 (The term "JP-A" as used herein means an "unexamined published Japanese patent application"). A typical dry analytical multilayer element is composed of a transparent support, a reagent layer, a reflecting layer and a spreading layer. More specifically, the reagent layer which is coated on the transparent support e.g., a thin plastic film provided with an undercoat, contains a reagent reactive with an analyte contained in a liquid sample, to produce a color having an optical density proportional to the analyte concentration. The reflecting layer functions to prevent light incident upon the reagent layer, from reaching the spreading layer, and thereby removes the influence of the liquid sample spotted on the spreading layer, on the optical measurement of the reagent layer. The spreading layer uniformly spreads a spotted liquid sample in a circular area approximately proportional to the amount of the liquid. In the quantitative analysis using such a dry analysis element, a prescribed amount of liquid sample, e.g., whole blood, is dropped on the surface of a spreading layer. The blood sample thus spread out in the spreading layer, passes through a reflecting layer, and reaches a reagent layer. In the reagent layer, reaction with the reagent takes place to produce a color. After spotting, the chemical analysis slide is kept at a constant temperature for a proper time to allow the color-producing reaction proceed sufficiently, and then the reagent layer is irradiated with light from the transparent support side. The quantity of reflected light is measured in a particular wavelength region to determine the reflection density, and to allow a quantitative analysis on the basis of a calibration curve determined in advance.

In many chemical analyses, whether carried out in accordance with wet or dry processes, erythrocyte-removed blood serum or blood plasma has been used as a sample. However, since separation of whole blood into erythrocytes and other components is laborious and costly, it is desirable that the analysis be carried out using undiluted whole blood as the sample.

In order to effect dry chemical analysis using whole blood as the sample, it is necessary to effectively separate the blood corpuscles (erythrocyte and leucocyte) and other high molecular components from the whole blood within the analytical element. One such means is to provide a filtering layer as disclosed in JP-B-No. 53-21677. However, as described in JP-A-No. 60-111960, it takes very long time to remove blood corpuscles from whole blood with a filtering layer provided inside the dry analytical element. Moreover, the blood plasma or serum obtained may lose part of the analyte in the filtering layer resulting in an incorrect analysis.

The dry analysis element disclosed in JP-B-No. 61-61347 is well suited for analysis of a particular component in whole blood because erythrocytes are separated and removed from the whole blood inside the spreading layer which is made of a fibrous material provided at the upper face of the analytical element, and the analyte contained in the resulting blood plasma diffuses rapidly into the reagent layer. However, in analysis of whole blood samples using the foregoing multilayer analytical element, considerable differences arose among the analytical results depending on the hematocrit values (volume percentage of blood corpuscles contained in whole blood) of the samples used, even if the plasma components has the same content in every blood sample. Particularly, when analyte concentrations in the blood are high, the data obtained often exhibited negative errors to the true concentrations in the blood plasma.

SUMMARY OF THE INVENTION

This invention provides a dry analysis element which avoids the interference from erythrocyte in whole blood, ensures rapid diffusion of an analyte in blood plasma into its reagent layer, and thereby makes it feasible to analyze a particular component in whole blood sample with high accuracy, irrespective of the hematocrit value of the blood.

In particular, the present invention presents the negative errors which have been present in analyte concentration data when the analytes are contained in high concentrations in whole blood having a high hematocrit value.

We have discovered that this can be achieved by providing an error preventing effective amount of cholic acid, deoxycholic acid, or salts thereof the porous spreading layer of a dry analysis element used in determining a particular component in blood from which the erythrocytes are not removed. The analytical element has at least two water permeable layers which include a reagent layer and said porous spreading layer, the reagent layer being arranged on the side opposite to the liquid accepting face of said porous spreading layer, and which contains a reagent composition capable of producing an optically detectable substance in the presence of the analyte in at lest one of the water permeable layers.

Preferably, the porous spreading layer contains an alkali metal salt of deoxycholic acid.

The dry analytical element of this invention may have no support, but preferably have the above-described water permeable layers on a water impermeable transparent support. Also, the water permeable layers may be provided on a water permeable support.

DETAILED DESCRIPTION OF THE INVENTION

The dry analytical element to be used in this invention comprises at least a water permeable reagnet layer and a water permeable porous spreading layer. In addition to these two layers, it may have another water permeable layer. Other water permeable layers may be sandwitched in between the reagent layer and the porous spreading layer.

The porous spreading layer is preferably a layer having a liquid metering function. The term "liquid metering function" refers to the ability to spread out a liquid sample spotted on the surface in the horizontal direction in a constant quantity per unit area without unevenly distributing any components contained in the sample. The porous spreading layer may be either fibrous or nonfibrous.

A reagent composition means a composition capable of producing a substance, such as, a dye, detectable, e.g., by optical means, in the presence of an analyte. At least part of the reagent composition is preferably contained in a reagent layer.

Cholic acids or deoxycholic acids which can be used in this invention include at least one compound selected from the group consisting of cholic acid, lithocholic acid, taurocholic acid, glycocholic acid, deoxycholic acid, chenodeoxycholic acid, taurodeoxycholic acid, glycodeoxycholic acid, and their salts, e.g., salts of alkali metals, such as, sodium, potassium, etc. Of these compounds, the alkali metal salts of deoxycholic acid, e.g., sodium deoxycholate, are preferred.

Preferably, the amount of the cholic acid, deoxycholic acid or salt thereof in the porous spreading layer ranges from 0.5 to 6 g/m$^2$, and preferably from 1 to 4 g/m$^2$.

The dry analysis element used in this invention can have various constructions. For instance, those described in U.S. Pat. No. 3,992,158, JP-A-No. 55-164356, and JP-A-No. 62-138756, JP-A-No. 62-138757 and JP-A-No. 62-138758 are suitable. When a light transmitting support is used, dry analysis elements which can be used in this invention include the following constructions:

(1) one which has a reagent layer on a support, and a liquid spreading layer on the reagent layer, (2) one which has on a support, a detecting layer, a reagent layer, and a liquid spreading layer, in this order, (3) one which has on a support, a reagent layer, a light reflecting layer, and a liquid spreading layer, in this order, (4) one which has on a support, a detecting layer, a reagent layer, a light reflecting layer, and a liquid spreading layer, in this order, (5) one which has on a support, a detecting layer, a light reflecting layer, a reagent layer, and a liquid spreading layer, in this order, (6) one which has on a support, a second reagent layer, a light reflecting layer, a first reagent layer and a spreading layer, in this order, and wherein a water absorbing layer may be provided between the support and the second reagent layer, and (7) one which has one a support, a second reagent layer, a first reagent layer and a spreading layer, in this order, and wherein a water absorbing layer may be provided between the support and the second reagent layer.

In these embodiments, the support may have a subbing layer.

The detecting layer is, in general, a layer which retains a dye or the like produced in the presence of the analyte, and which diffuses into it, and enables the optical detection of the dye through the light transmitting support. It can be made up of a hydrophilic polymer, and may contain a mordant, e.g., a cationic polymer, in the case of anionic dyes.

Preferably, layer construction is used with the present invention constructions (1), (2) or (7), a protein blocking layer may be provided between the reagent layer and the spreading or detecting layer. In foregoing constructions (3) to (6), a protein blocking layer may be provided between the light reflecting layer and the detecting, reagent or spreading layer, between the reagent layer and the detecting layer, or between the reagent layer and the spreading layer.

(1), (3) or (7), a water absorbing layer may be provided between the support and the reagent layer. The water absorbing layer refers generally to a layer into which a dye produced in the presence of an analyte cannot significantly diffuse, and which can be composed of a swellable hydrophilic polymer. Also in constructions (6) or (7), a protein blocking layer may be provided between the second reagent layer and the first reagent layer between the first reagent layer and the spreading layer, or between the light reflecting layer and the first or the second reagent layer.

A desirable material for a water impermeable transparent support is polyethylene terephthalate. Also, cellulose esters, such as, cellulose triacetate may be used. Such a support is, in general, provided with a subbing layer or rendered hydrophilic to firmly adhere a hydrophilic layer thereto.

A reagent composition comprises constituents capable of producing an optically detectable substance, such as, a dye, in the presence of an analyte. For instance, compositions capable of producing dyes by oxidation of leuco dyes, e.g., arylimidazole leuco dyes as disclosed in U.S. Pat. No. 4,089,747 and JP-A-No. 59-193352, diazonium salts, compositions containing compounds capable of producing dyes by coupling with other compounds when oxidized, e.g., 4-aminoantipyrins, and phenols or naphthols, compositions comprising compounds capable of producing dyes in the presence of reduction type coenzymes and an electron transfer agent, and the like can be employed.

For analysis elements for the determination of enzyme activity, on the other hand, a self-developing substrate capable of liberating a colored substance, such as, p-nitrophenol, can be contained in the reagent layer and/or the spreading layer.

Constituents of the reagent composition may be present together in one water permeable layer, e.g., a reagent layer, or divided into separate layers. In one example of the latter case, constituents taking part in production of an intermediate by the reaction of an analyte with a reagent, are contained in a reagent layer, and constituents producing a dye or the like by reaction with the intermediate, e.g., indicator, are contained in the second reagent layer, provided between the reagent layer and the support. In another example, the constituents producing the intermediate are contained in the blood corpuscle filtering layer or the light reflecting layer, and the indicator is contained in the reagent layer. Moreover, a gas permeable layer and an obstacle removing layer, e.g., as disclosed in U.S. Pat. No. 4,066,403, corresponding to JP-B-No. 58-19062, may be provided between the first and the second reagent layers. These layers may be impermeable to water, if needed.

Part or all of the constituents of the reagent composition may be in a substantially homogeneous layer containing a hydrophilic polymer as a binder. Gelatin and derivatives thereof, e.g., phthaloylated gelatin, cellulose derivatives, e.g., hydroxyethylecllulose, agarose, acrylamide polymers, methacrylamide polymers and copolymers of various vinyl monomers and acrylamide or methacrylamide can be used for the hydrophilic polymer.

Part or all of the constituents of the reagent composition may be in a porous layer. Fibrous porous layers, e.g., filter paper, nonwoven fabrics, etc., as well as nonfibrous porous layer may be used as the reagent layer. Preferable nonfibrous porous layers include layers made of blush polymers, including cellulose esters, such as, cellulose acetate, cellulose acetate/butyrate and cellulose nitrate, as disclosed, e.g., in JP-B-No. 53-21677 and U.S. Pat. No. 1,421,341; microporous layer, of polysulfones disclosed in JP-A-No. 62-27006 and Japanese Patent Application No. 63-10452; and porous layers having capillary pores formed by binding polymer fine particles, glass particles, diatomaceous earth or the like with hydrophilic or water nonabsorbing polymer as is disclosed in JP-B-No. 53-21677 and JP-A-No. 55-90859.

Incorporation of a reagent composition, into a porous layer can be effected by fixing a porous spreading layer impregnated or coated with a proper solution or dispersion of the reagent composition on another water permeable layer, e.g., a reagent layer, in accordance with a method as disclosed in JP-A-No. 55-164356. Also, a porous layer may first be fixed on another water permeable layer, e.g., a subbing layer, an adhesive layer, a water absorbing layer, using the foregoing method, as disclosed in JP-A-No. 55-164356, and then a solution or dispersion of the reagent composition may be applied to the porous layer.

In saturating or coating a porous layer with a reagent composition or a part thereof, known processes can be used. As for the coating process, dip coating, doctor coating, hopper coating, curtain coating or so on can be chosen at discretion.

In addition, it is feasible to incorporate a reagent composition into a porous layer by forming a reagent composition-containing homogeneous layer using a hydrophilic polymer as a binder, and then fixing a reagent composition-free porous layer on the homogeneous layer according to the method disclosed in JP-A-No. 55-164356.

A reagent composition can contain an activator, a buffer, a hardener, a surfactant and the like, if desired. Examples of buffers include carbonates, borates, phosphates, and Good's buffers as described in *Biochemistry*, vol. 5, No. 2, pp. 467–477 (1966). Buffers can also be chosen by reference to Buichi Horio et al., *Tanpakushitu-Koso no Kiso Jikkenho* (which means "methods for basic experiments on protein and enzyme"), Nankodo, Tokyo (1981), *Biochemistry*, supra, and so on.

The content of each constituent in the above-described reagent compositions or the amount of reagent can be changed depending on the analyte to be determined. These quantities are easily determined to those skilled in the arts.

Reagent compositions containing enzymes may be used in this invention. Examples of such compositions include those disclosed in Japanese Patent Application No. 60-279859, pp. 18–20. On the other hand, reagent compositions may contain constituents which exhibit or quench fluorescence in the presence of an analyte.

Examples of fibrous porous spreading layers include filter paper, non-woven fabric, textile fabrics, e.g., plain weave texture, knitted cloth, e.g., tricot knitting, fibrous glass filter paper, and the like. Of these materials, textured and knitted fabrics are preferred. Texture fabrics and the like may be subjected to a glow discharge treatment, as disclosed in JP-A-No. 57-66359. For the purpose of controlling the spreading area, spreading speed and the like, the spreading layer may contain a hydrophilic polymer or a surfactant, as disclosed in JP-A-No. 60-222770, and Japanese Patent Application Nos. 61-122875, 61-122876 and 61-143754.

When a nonfibrous porous layer is used as spreading layer, the layer is preferably made of a blush polymer including cellulose esters as disclosed, e.g., in JP-B-No. 53-21677 and U.S. Pat. No. 1,421,341, such as cellulose acetate, cellulose acetate/butyrate and cellulose nitrate. In addition, a microporous film of a polyamide, such as, 6-nylon or 6, 6-nylon, polyethylene, polypropylene, or the like may be used. Also suitable are microporous layers of polysulfone disclosed in JP-A-No. 62-7006, and porous layers having continuous pores formed by binding polymer fine particles, glass particles, diatomaceous earth or the lie, with a hydrophilic or water nonabsorbing polymer.

An adhesive layer for adhering a porous layer to be laminated may be provided on a support, a subbing layer, a water absorbing layer, a detecting layer or so on. The adhesive layer is preferably made up of a hydrophilic polymer which swells in water to fix the porous layer, e.g., gelatin, a gelatin derivative, polyacrylamide, starch or the like.

A porous layer can be fixed on another porous layer or a nonporous layer with an adhesive. However, it is necessary to make certain that the adhesive does not significantly inhibit the uniform permeation of liquid and analyte. For this purpose, the adhesive is coated discontinuously, and fine penetration holes are formed in those areas with no adhesive. This discontinuous coating can be effected by the method disclosed in JP-A-No. 62-138756.

A light reflecting/shielding layer can shield the red color of hemoglobin in the erythrocytes of whole blood, and functions as light reflecting layer or a background layer in performing the reflection photometry of a detectable change, e.g., a change in color, color production, etc., which takes place in the detecting layer, reagent, layer or the like, from the side of the light permeable support. A nonporous or porous layer in which light reflecting particles, such as, titanium oxide, barium sulfate, etc., are dispersed using a hydrophilic polymer as a binder can be used as a light reflecting/shielding layer. Materials suitable for the binder include gelatin, gelatin derivatives, polyacrylamides and the like. In addition, light reflecting particles-containing microcapsules as disclosed in Japanese Patent Application No. 63-9046 are useful for the light reflecting/shielding layer.

In order to analyze erythrocyte-containing blood with the analysis element of this invention, a specific, e.g., from 3 to 30 microliters of sample liquid is spotted on the dry analysis element, and the resulting analysis element is incubated (heated) at a prescribed temperature for a definite time in a proper thermostat or colorimeter. The element is then subjected to photometry at regular intervals. In the analysis, a method for detecting an optical change taking place at the substantial end point of the reaction of a particular constituent in the sample with a reagent in the analysis element, as well as a method of determining a reaction rate from the color-developing speed or the like on the way to conclusion of reaction can be utilized.

For measurements of spectral reflection densities, known apparatuses can be used, e.g., those disclosed in U.S. Patents 4,488,810, 4,584,275, JP-A-No. 61-294367, JP-A-No. 61-294368, JP-A-No. 62-184335, JP-A-No. 62-184336, JP-A-No. 62-198736, JP-A-No. 62-245141, JP-A-No. 62-245142, JP-A-62-245143, Japanese Patent Application Nos. 61-25582, 61-25583, 61-109402, and 61-207045 to 61-207048, and JP-A-No. 62-299769, JP-A-No. 63-40839, JP-A-No. 63-40840, JP-A-No. 62-276439 and JP-A-No. 63-61958; Fuji Drychem 1000, Fuji Drychem 2000 and Fuji Drychem 5000 analyzers (produced by Fuji Photo Film Co., Ltd.); and Ektachem 400, Ektachem 700 and Ektachem DT-60 analyzers (produced by Eastman Kodak Company).

This invention can be applied, not only to the determination of low molecular constituents in whole blood, e.g., glucose, urea, uric acid, creatinine, etc., but also the determination of high molecular constituents, e.g., total protein, albumine, various enzymes, etc., or constituents bonded to protein, such as, bilirubin. This invention is well-suited to determine an analyte whose concentration is about the same as that blood corpuscles, or whose concentration in blood plasma is ½ to 3 times that is the blood corpuscles. In particular, this invention is useful for those cases in which saccharides, such as, glucose, are contained in high concentrations.

Moreover, when either an antigen or antibody is incorporated into a porous layer, this invention can be used for the determination of the antigen or antibody using immunological processes.

In accordance with this invention, whole blood is used as a sample, and the analysis element can determine various kinds of analytes without any appreciable influence due to the hematocrit value of the blood, which may over the wide range of 25% to 70%. In particular, when the whole blood used as a sample has a hematocrit value in the wide range of 25% to 70%, a difference of determined values from the data obtained by using whole blood samples having their hematocrit values in the range of 40% to 50% is practically negligible.

EXAMPLE 1

(1) Support and Second Reagent Layer

The following ingredients were coated in the form of a water solution onto a 180 micron-thick smooth film of colorless transparent polyethylene terephthalate (PET), provided with a gelatin subbing layer so as to have the respective coverages described below, and then dried (Second reagent layer).

Coating Composition of Second Reagent Layer

| | |
|---|---|
| Gelatin | 6.0 g/m$^2$ |
| 1,7-Dihydroxynaphthalene | 0.22 g/m$^2$ |
| 4-Amino-2, 3-dimethyl-1-phenyl-3-pyrazoline-5-one | 0.40 g/m$^2$ |

(2) First Reagent Layer

The following ingredients were coated in the form of a water solution on the second reagent layer so as to have the respective coverages described below, and dried (First reagent layer).

Coating Composition of First Reagent Layer

| | |
|---|---|
| Gelatin | 6.9 g/m$^2$ |
| Peroxidase | 23800 UNIT/m$^2$ |
| Glucose oxidase | 10100 UNIT/m$^2$ |
| Styrene/p-(1-methyl-1-piperazino)-ethyl styrene/divinylbenzene copolymer | 2.4 g/m$^2$ |
| Polyoxyethylene nonyl phenol (containing 40 oxyethylene units) | 0.60 g/m$^2$ |

(3) Light Reflecting/Shielding Layer

The following ingredients in the form of a water solution were coated on the first reagent layer so as to have the respective coverages described below, and dried to provide a light reflecting/shielding layer.

Coating Composition of Light Reflecting/Shielding Layer

| | |
|---|---|
| Titanium dioxide | 8.2 g/m$^2$ |
| Gelatin | 0.81 g/m$^2$ |
| Polyoxyethylene nonyl phenol (containing 40 oxyethylene units) | 0.23 g/m$^2$ |

(4) Adhesive Layer

The following ingredients in the form of a water solution were coated on the light shielding layer so as to have the respective coverage described below, and dried to provide an adhesive layer.

Coating Composition of Adhesive Layer

| | |
|---|---|
| Gelatin | 1.5 g/m$^2$ |
| Polyoxyethylene nonyl phenol (containing 40 oxyethylene units) | 0.22 g/m$^2$ |
| Calcium acetate | 0.52 g/m$^2$ |

(5) Spreading Layer

The following composition, warmed at 45° C., was applied to the whole surface of the adhesive layer at a coverage of about 30 g/m$^2$ to make the adhesive layer swell, and then a tricot knit cloth made of polyester yarn was married to the swolled adhesive layer, and the combined layers were passed between rolls and dried to laminate them.

| | |
|---|---|
| Water | 97.8 g |
| N-(Pyrrolidinochloromethyl) pyrrolidinium-β-naphthalenesulfonic acid | 2.0 g |
| Polyoxyethylene nonyl phenol (containing | 0.2 g |

-continued 40 oxyethylene units)

Thereafter, a 7% water solution of sodium deoxycholate was coated on the knit cloth at a coverage of 2.1 g/m², and dried to prepare an analysis element (1) for glucose determination.

For the purpose of comparison, an analysis element (2) was prepared in the same manner as described above, except that the coating of the sodium deoxycholate solution on the knit cloth was omitted.

Analysis of Glucose in Whole Blood

Glucose was added to fresh whole blood gathered from a person in an amount necessary to adjust the glucose concentration to 540 mg/dl, and allowed to stand for 30 minutes at room temperature. Thereafter, a part of the whole blood was centrifuged to separate it into corpuscles and plasma. The thus obtained whole blood, corpuscles and plasma were mixed in proper ratios to prepare whole blood samples having hematocrit values of 15%, 25%, 40%, 55% and 70%, respectively. The accurate glucose concentrations in these samples were determined by the glucose electrode method. Each of four kinds of whole blood samples was spotted in amounts of 10 microliters each on separate spreading layers of the foregoing analysis elements (1) and (2), and incubated at 37° C. for 6 minutes. The thus processed analysis elements were examined for optical reflection densities by reflection photometry from the support side with visible light whose main wavelength was 540 nm. Glucose concentrations in the four kinds of blood samples were determined from the thus measured reflection densities and calibration curves made in advance for the two different analysis elements using standard blood samples prepared by adding varied amounts of glucose to whole blood having its hematocrit value adjusted to 40%. The results obtained are shown in Table 1.

TABLE 1

| Hematocrit Value (%) | 15 | 25 | 40 | 55 |
|---|---|---|---|---|
| Glucose Concentration (mg/dl) | | | | |
| Analysis Element (1) | 567 | 562 | 540 | 529 |
| Analysis Element (2) | 583 | 556 | 540 | 486 |

As can be seen from the data in Table 1, hematocrit value has a markedly small influence on the analysis element (1) prepared in accordance with this invention, compared with that on the analysis element (2) prepared for comparison. Thus, the analysis element of this invention provided glucose concentration data almost equal or very close to the value determined from the whole blood having the hematocrit value of 40%, even when whole blood having a hematocrit value lower than 40% or higher than 50% was used as the sample.

While the invention has been described in detail and with reference to specific embodiments thereof, it will be apparent to one skilled in the art that various changes and modifications can be made therein without departing from the spirit and scope thereof.

What is claimed is:

1. A dry analysis element for the determination of a component in erythrocyte-containing blood which comprises at least two water permeable layers which include a reagent layer and a porous spreading layer having a liquid-accepting face, the reagent layer being arranged on the side opposite to the liquid-accepting face for the porous spreading layer, and containing a reagent composition capable of producing an optically detectable substance in the presence of an analyte in at least one of the water permeable layers, said porous spreading layer containing a compound selected from the group consisting of cholic acids, deoxycholic acids, and salts thereof, said compound being present in an amount effective to substantially prevent analysis errors due to variation in the hematocrit value of a blood sample.

2. The analysis element of claim 1 wherein said porous spreading layer contains an alkali metal salt of deoxycholic acid.

3. The analysis element of claim 1 wherein the compound is selected from the group consisting of cholic acid, lithocholic acid, taurocholic acid, glycocholic acid, deoxycholic acid, chenodeoxycholic acid, taurodeoxycholic acid, glycodeoxy-cholic acid, and their salts.

4. The analysis element of claim 3 wherein the salt is an alkali metal salt.

5. The analysis element of claim 4 wherein the alkali metal salt is selected from the group consisting of sodium and potassium.

6. The analysis element of claim 1 wherein the amount of said compound is from about 0.5 to 6 g/m².

7. The analysis element of claim 6 wherein the amount of said compound is from about 1 to 4 g/m².

8. In a method for the analysis of a component in an erythrocyte-containing blood sample wherein a droplet size sample of the blood is introduced to a dry analysis element and the quantity of the component is determined by optical analysis, the improvement which comprises said element having at least two water permeable layers which include a reagent layer and a porous spreading layer having a liquid-accepting face, the reagent layer being arranged on the side opposite to the liquid-accepting face of the porous spreading layer, and containing a reagent composition capable of producing an optically detectable substance in the presence of an analyte in at least one of the water-permeable layers, said porous spreading layer containing a compound selected from the group consisting of cholic acids, deoxycholic acids, and salts thereof, said compound being present in an amount effective to substantially prevent analysis errors due to variation in the hematocrit value of a blood sample.

9. The method of claim 8 wherein non-hydrophobic constituents in blood are determined.

10. The method of claim 8 wherein saccharides in blood are determined.

11. The method of claim 8 wherein glucose in blood is determined.

12. The method of claim 8 wherein said porous spreading layer contains an alkali metal salt of deoxycholic acid.

13. The method of claim 8 wherein the compound is selected from the group consisting of cholic acid, lithocholic acid, taurocholic acid, glycocholic acid, deoxycholic acid, chenodeoxycholic acid, taurodeoxycholic acid, glycodeoxycholic acid, and their salts.

14. The method of claim 8 wherein the salt is an alkali metal salt.

15. The method of claim 8 wherein the alkali metal salt is selected from the group consisting of sodium and potassium.

16. The method of claim 8 wherein the amount of said compound is from about 0.5 to 6 g/m².

17. The method of claim 8 wherein the amount of said compound is from about 1 to 4 g/m².

18. The method of claim 8 wherein the blood to be analyzed has a hematocrit value in the range from about 25 to 70%.

* * * * *